United States Patent [19]

Rosowsky

[11] Patent Number: 5,234,925
[45] Date of Patent: Aug. 10, 1993

[54] 2-AZA-2-DESAMINO ANALOGUES OF 5,8-DIDEAZAFOLIC ACID

[75] Inventor: Andre Rosowsky, Needham, Mass.

[73] Assignee: Dana-Farber Cancer Institute, Inc., Boston, Mass.

[21] Appl. No.: 744,917

[22] Filed: Aug. 14, 1991

[51] Int. Cl.$^5$ .................. C07D 253/08; C07D 409/12; C07D 417/12; A61K 31/53
[52] U.S. Cl. ..................................... 514/243; 544/183
[58] Field of Search ........................ 544/183; 514/243

[56] References Cited

U.S. PATENT DOCUMENTS

| | | | |
|---|---|---|---|
| 3,678,166 | 7/1972 | Kathawala | 424/246 |
| 3,794,726 | 2/1974 | Ariyan | 424/249 |
| 3,818,001 | 6/1974 | Kathawala | 260/247.7 |
| 3,876,638 | 4/1975 | Oswald et al. | 260/248 |
| 4,680,293 | 7/1987 | Wright, Jr. et al. | 514/243 |
| 4,956,461 | 9/1990 | Rosowsky | 544/258 |

OTHER PUBLICATIONS

Acharya and Hynes, J. Heterocyclic Chemistry 12:1283-1286, (1975).
Bird et al., Molecular Pharmacology 6:573-575, 1970.
Calvert et al., Europ. J. Cancer 16:713-722, 1980.
Cheng et al., Cancer Research 45:598-600, 1985.
Davoll et al., J. Chem. Soc. Section C:997-1002, 1970.
Hughes et al., J. Med. Chem. 33:3060-3067, 1990.
Hynes et al., J. Med. Chem. 30:1515-1519, 1987.
Hynes et al., J. Med. Chem. 31:449-454, 1988.
Jackman et al., J. Med. Chem. 33:3067-3071, 1990.
Jackman et al., American Association for Cancer Research 31:342:2023, 1990.
Jackman et al., Cancer Research 50:5212-5218, 1990.
Jones et al., Europ. J. Cancer 16:707-711, 1980.
Jones et al., Europ. J. Cancer 17:11-19, 1981.
Jones et al., J. Med. Chem. 28:1468-1476, 1985.
Jones et al., J. Med. Chem. 29:468-472, 1114-1118, 1986.
Jones et al., J. Med. Chem. 32:847-852, 1989.
Jones et al., J. Heterocyclic Chem. 26:1501-1507, 1989.
Marsham et al., J. Med. Chem. 32:569-575, 1989.
Marsham et al., J. Med. Chem. 33:3072-3078, 1990.
Marsham et al., J. Med. Chem. 34:1594-1605, 1991.
Montfort et al., Biochemistry 29:6964-6977, 1990.
Moran et al., Molecular Pharmacology 36:736-743, 1989.
Nair et al., J. Med. Chem. 26:604-607, 1983.
Oatis and Hynes J. Med. Chem. 20:1393-1396, 1977.
Rosowsky et al., J. Med. Chem. 34:227-234, 1991.
Sessa et al., Eur. J. Cancer Clin. Oncol. 24:769-775, 1988.
Thornton et al., J. Med. Chem. 34:978-984, 1991.

*Primary Examiner*—John M. Ford
*Attorney, Agent, or Firm*—Fish & Richardson

[57] ABSTRACT

2-Aza-2-desamino analogues of 5,8-dideazafolic acid, which analogues have the formula

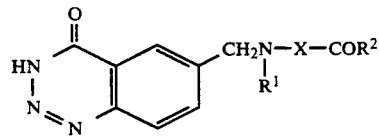

wherein
X is an aryl or heteroaryl moiety;
$R^1$ is H, $C_1$-$C_4$ alkyl, $C_3$-$C_4$ alkenyl, or $C_3$-$C_4$ alkynyl; and
$R^2$ is OH, an L-α-amino acid, or a peptide comprising L-α-amino acids.

11 Claims, 1 Drawing Sheet

SCHEME Ia aReagents: (i) SOCl₂/MeOH; (ii) NH₃; (iii) H₂/Pd-C; (iv) NaNO₂/HCl;
(v) N-bromosuccinimide/AcOH/hv; (VI) 4R¹NH
C₆H₄CONHCH(COOMe)CH₂CH₂COOMe; (vii) NaOH SCHEME IIa aReagents: (i) R¹NH X COOH (ii) protected amino acid+ coupling reagent;
(iii) deprotection reagent

2-AZA-2-DESAMINO ANALOGUES OF 5,8-DIDEAZAFOLIC ACID

This invention was made in the course of work supported in part by the U.S. Government, which therefore has certain rights in the invention.

The field of the invention is folic acid analogues.

BACKGROUND OF THE INVENTION

Methotrexate (MTX) is a classical antifolate drug used for many years in the treatment of human cancers. This drug exerts its primary biological effect by inhibiting dihydrofolate reductase (DHFR), an enzyme which is responsible for the terminal step in converting the vitamin folic acid into a reduced form that actively participates in several crucial metabolic pathways within cells. The usefulness of MTX as a cancer chemotherapeutic, however, is often limited by intrinsic or acquired resistance of tumor cells to its effects, so that alternative antifolates effective against MTX-resistant tumors have been sought.

The potential therapeutic significance of folic acid analogues targeted against thymidylate synthase (TS) as opposed to DHFR was predicted more than 20 years ago by Borsa et al. (Cancer Res. 29:737, 1969). Shortly thereafter, the potent biological activity of 5,8-dideazafolic acid (1) was reported (Hutchison et al., Proc. Amer. Assoc. Cancer Res. 10:80, 1969; Bird et al., J. Mol. Pharmacol. 6:573, 1970). This led to an extensive program of synthesis of quinazoline analogues, and to the eventual selection of the $N^{10}$ propargyl derivative 2 (CB3717, PDDF) as a suitable candidate for biochemical and clinical evaluation. While this compound has many desirable evaluation. While this compound has many desirable pharmacological characteristics, such as the ability to enter cells by a transport mechanism distinct from that of reduced folates and MTX, its clinical usefulness is hampered by hepatic and renal toxicities, which are due in part to low solubility at physiologic pH.

The toxicity problems encountered during clinical trials with CB3717 prompted a vigorous search for more soluble congeners, culminating in the discovery of a second-generation family of folate-based TS inhibitors, of which the prototypical example was 2-desamino-5,8-dideazafolic acid (3) and its $N^{10}$-methyl (4) and $N^{10}$-propargyl (5) analogues (Marsham et al., J. Med. Chem. 32:569, 1989; Jones et al., J. Med. Chem. 32:847, 1989). Also active were the corresponding 2-desamino-2-methyl analogues 6-8 and some of their congeners.

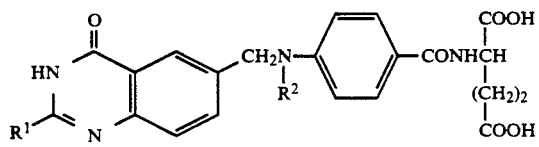

1,2: $R^1 = NH_2$, $R^2 = H$, $CH_2≡CCH$
3-5: $R^1 = H$, $R^2 = H$, Me, $CH_2C≡CH$
6-8: $R^1 = Me$, $R^2 = H$, Me, $CH_2C≡CH$

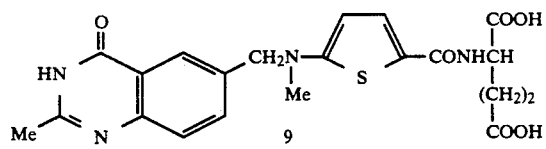

Biochemical studies with compounds 3-8 revealed that while replacement of the $NH_2$ group at $C^2$ by H or methyl generally results in weaker binding to purified TS in vitro, it also results in increased inhibitory potency against intact cells in culture (Jackman et al., Cancer Res. 50:5212, 1990; Jones et al.; Hughes et al., J. Med. Chem. observations are explained by the findings that (i) deletion of the 2-amino group does not diminish the analog's substrate activity for folylpoly-glutamate synthetase (FPGS), and (ii) polyglutamylation of the 2-desamino compounds increases binding to TS by as much as 100-fold (Moran et al., Mol. Pharmacol 36:7836, 1989; Jackman et al.). On this basis, a large number of congeners modified at $C^2$, $N^{10}$, and the aroyl moiety were synthesized to permit a detailed structure-activity analysis of 2-desamino-5,8-dideazafolates relative to the parent 2-amino compounds. The thiophene analogue 9 (ICI-D1694), with a methyl group at $C^2$ and a methylated $N^{10}$ emerged from these studies as the most promising desamino compounds for further evaluation (Jodrell et al., Proc. Amer. Assoc. Cancer Res. 31:341, 1990; Marsham et al., J. Med. Chem. 34:1594, 1991).

SUMMARY OF THE INVENTION

The folate analogues of the invention are those of general structure A (illustrated below), in which $C^2$ and the associated H or methyl substituent of the standard desamino-5,8-dideazafolic acid compound have been replaced by nitrogen and a lone electron pair. These changes were made on the theory that (i) removal of H or Me might enable the molecule to extend more deeply into the active site pocket of the enzyme, and (ii) $N^2$ might interact with active site residues by H-bonding, either directly or via a molecule of ordered water. Both of these properties were expected to be favorable for TS binding. Furthermore, since the compounds of the invention have been found to be good FPGS substrates and their polyglutamates are likely to show the same increase (100-fold or more) in TS binding as that resulting from polyglutamylation of the more conventional 2-desamino from polyglutamylation of the more conventional 2-desamino and 2-desamino-2-methylquinazolines (e.g., 3 and 6), a high degree of in vivo anticancer activity is anticipated.

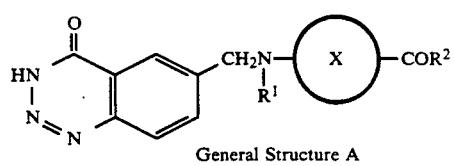

General Structure A $R^1 = H$   X = aryl or   $R^2 = $ L-glutamic acid,
alkyl      heteroaryl    other α-amino acids,
alkenyl    moiety        or their derivatives
alkynyl By "aryl moiety" is meant an aromatic monocylic or condensed polycyclic system containing only carbon atoms in the ring itself; "heteroaryl" is an aromatic monocyclic or condensed polycyclic system which has one or more heteroatoms (e.g., O, N, or S) in the ring.

In preferred embodiments, $R^1$ of general structure A is H, $C_4$-$C_4$ alkyl (e.g., —$CH_3$ or —$CH_2CH_3$), $C_3$-$C_4$ alkenyl (e.g., —$CH_2CH=CH_2$), or $C_3$-$C_4$ alkenyl (e.g., —$CH_2C\equiv CH$); $R_2$ may be OH, an L-α-amino acid such L-glutamic acid or L-aspartic acid, or a peptide comprising L-α-amino acids (such as poly-L-glutamic acid); and X is thiophene

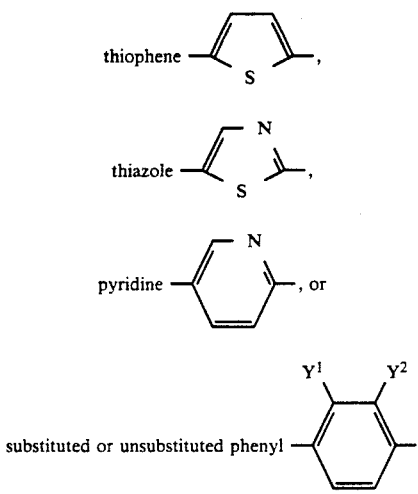

wherein each of $Y^1$ and $Y^2$, independently, is H, methyl, ethyl, or a halogen. More preferably, $Y^1$ is H and $Y^2$ is H, methyl, ethyl, F, Cl, or Br (most preferably H). Specific examples of compounds of the invention include:

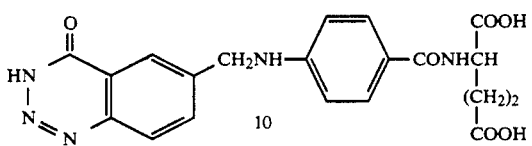

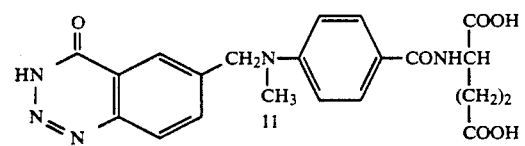

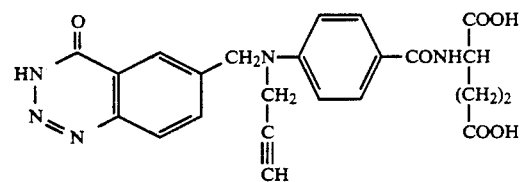

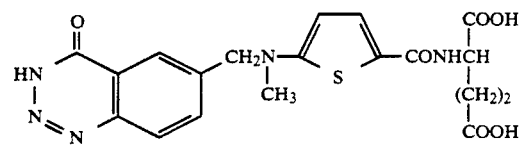

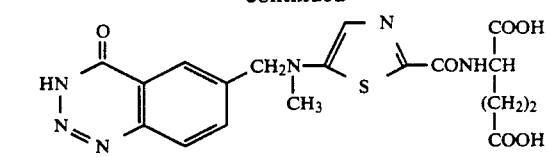

The compounds of the invention are potent inhibitors of DNA synthesis in mammalian cells, such as in cultured cells or in animals (e.g., humans). By inhibiting the conversion by the enzyme TS of dUMP into dTMP, a precursor necessary for DNA synthesis, the rate of DNA synthesis in treated cells is retarded; if the cell cannot replicate its genome, it cannot proliferate. Thus, the compound is useful for treating an animal (e.g., a mammal) having a condition, such as cancer or psoriasis, characterized by overproliferation of cells. Such a treatment would be accomplished by introducing into the animal (e.g., by intravenous injection, or insertion of a biodegradable implant) an amount of the compound of the invention sufficient to reduce the rate of proliferation of the target cells. This amount would be determined in the course of preclinical and clinical trials of the subject compound, using standard protocols for such trials. Guidance in this regard is provided by published reports concerning the dosage of other folic acid analogues previously tested in animals (including human patients) necessary to detect an antitumor effect (see, for example, Sessa et al., Eur. J. Cancer Clin. Oncol. 24:769-775, 1988; Calvert et al., Eur. J. Cancer 16:713-722, 1980; Jackman et al., Cancer Research 50:5212-5218, 1990; Oatis and Hynes, J. Med. Chem. 20:1393-1396, 1977; and Jones et al., Eur. J. Cancer 17:11-19, 1981, each of which publications is herein incorporated by reference). It is expected that a useful dosage will be between 1.0 and 100 mg/kg, with 10-50 mg/kg being the preferred range; determination of the exact dosage will be readily determined by one of ordinary skill in the art of pharmacology. In addition, the compound of the invention may also be combined with another antifolate, such as the non-polyglutamylatable dihydrofolate reductase (DHFR) inhibitor trimetrexate (cf. Galivan et al., Cancer Res. 48:2421, 1988; Galivan et al., J. Biol. Chem. 264:10685, 1989), in order to more completely block metabolism involving folic acid in the treated cells. Such a bivalent route of treatment could utilize separate injections of the two agents, or could combine the two agents in a single preparation.

DETAILED DESCRIPTION

The drawings are first described.

Drawings

Figure 1:
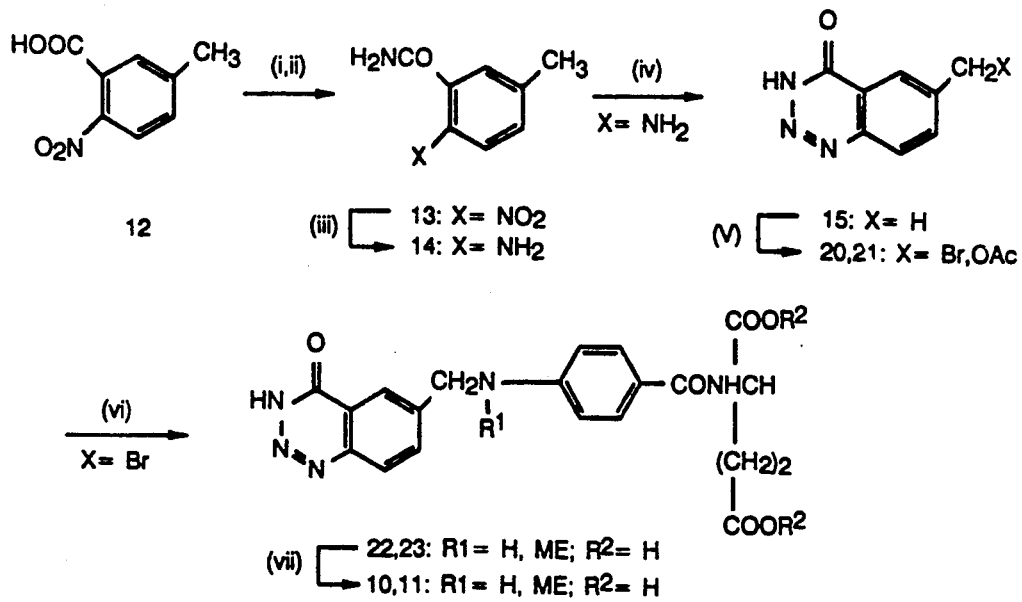
Figure 2:
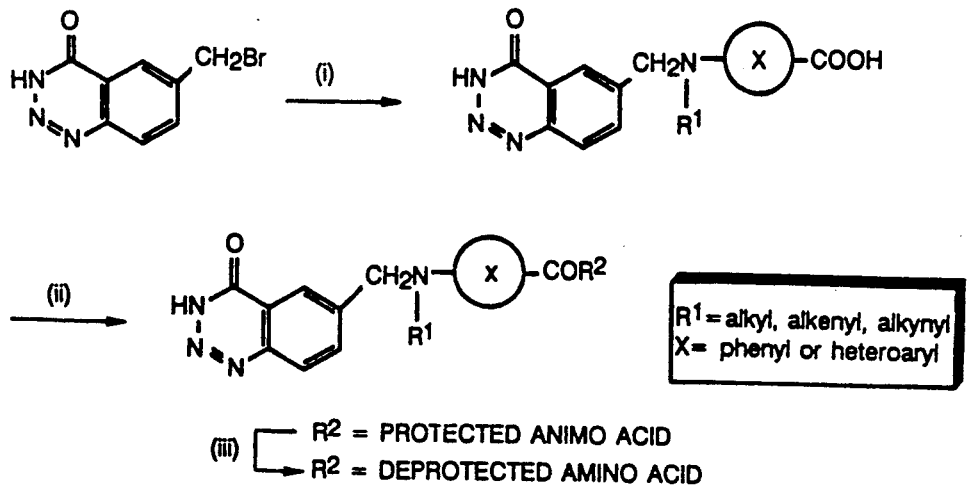

FIGS. 1 and 2 are representations of alternative schemes for synthesis of 10,11, and additional compounds of the invention. Described below is the synthesis of N-[4-[1,2,3-benzotriazin-4(3H)-on-6-yl]methylamino]benzoyl-L-glutamic acid (10, "2-aza-2-desamino-5,8-dideazafolic acid") and N-[4-[1,2,3-benzotriazin-4(3H)-on-6-yl]methyl]-N-methylamino]benzoyl-L-glutamic acid (11, "2-aza-2-desamino-$N^{10}$-methyl-5,8-dideazafolic acid"), the first two known members of the family embodied in general structure A, as well as methods for preparing other members of the family. Also presented is data showing that 10 is a potent TS inhibitor, is a substrate for FPGS, and inhibits the growth of cultured mammalian cells.

SYNTHESIS

Schemes I and II, shown in FIG. 1 and FIG. 2, respectively, outline a synthesis of 10 and 11 and an alternative general route by which additional members of the series, such as those with other alkyl, alkenyl, or alkynyl groups on $N^{10}$, or with a thiophene, thiazole, or pyridine ring in place of phenyl, are expected to be accessible. Sequential reactions of 5-methyl-2-nitrobenzoic acid (12) (Aldrich Chemical Co., Milwaukee) with thionyl chloride and methanol followed by ammonia afforded 5-methyl-2-nitrobenzamide (13, 87%), which On catalytic hydrogenation followed by treatment with nitrous acid (Ferrand et al., Eur. J. Med. Chem. 22:337, 1987) yielded 2-amino-5-methylbenzylamide (14, 96%) and 6-methyl-1,2,3-benzoriazine-4(3H)-one (15, 97%), respectively (Scheme I). Improved yields in the ring closure reaction were obtained by using less than the reported amount of acid. Confirmation of ring closure to a 1,2,3-benzotriazine-4(3H)-one came from the $^1$H-NMR spectrum, in which all three aromatic proton signals were markedly deshielded ($\delta 7.8$–8.0), in agreement with the powerful electron-withdrawing character of the triazinone moiety. Several attempts were made to protect $N^3$ in 15 in the expectation that solubilization would be necessary if subsequent benzylic bromination were done in $CCl_4$, the traditional solvent for such reactions. Treatment of the Na salt of 15 with pivaloyloxymethyl chloride in DMF afforded a single product which appeared to be the desired $N^3$-derivative 16. However, in contrast to the facile preparation of the corresponding pivaloyloxymethyl compound in the quinazoline series, all efforts to recrystallize 16 led to deacylation. We also attempted to prepare the $N^3$-acetyl derivative 17 by reaction of the Ag salt of 15 with acetyl chloride, as has been described for the analogue without a 6-methyl substituent (Gibson et al., J. Org. Chem. 22:337, 1987). To our surprise, the reaction of 15 yielded a product whose $^1$H-NMR spectrum contained two Me groups, but whose UV spectrum differed from the values expected from the literature (Murray et al., J. Chem. Soc. 1970:2070). Moreover, efforts to purify the product by silica gel chromatography led only to deacylation. Although definitive proof of its identity was not obtained, this material was tentatively assigned the O-acetyl structure 18. Finally, we tried to prepare 17 from the Na salt of 15 and acetic anhydride in DMF, but no reaction occurred at room temperature and the only product identified after heating was the benzoxazinone 19 (Murray et al.).

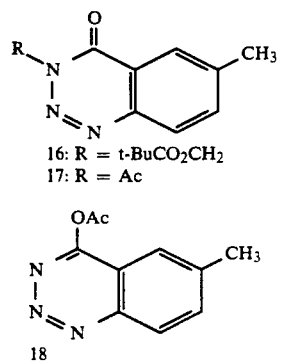

16: R = t-BuCO$_2$CH$_2$
17: R = Ac

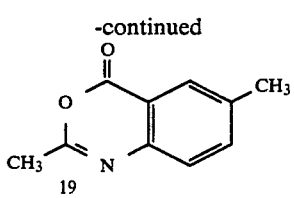

Bromination of 15 without protection of $N^3$ turned out to be possible by using hot acetic acid as the solvent for the benzotrizinone. The presence of the brominated product 20 was evident in the $^1$H-NMR spectru, which showed a downfield singlet at $\delta 4.63$ as compared with $\delta 3.30$ for the Me group in 15. Also present were two other singlets, which we believe correspond to 21, presumably formed by solvolysis of 20. Heating the crude bromination product (estimated from the $^1$H-NMR spectrum to contain roughly 40 mol % of 20) directly with dimethyl N-4-aminobenzoyl-L-glutamate and NaHCO$_3$ in warm DMF for 3 days afforded the protected diester 22 (45% crude yield), and further treatment of 20 for a few minutes with NaOH in aqueous MeOH afforded the diacid 10 (81%). The UV absorption spectrum of 10 showed a small bathochromic shift in going from acid to neutral to alkaline pH [$\lambda_{max}$(0.1M HCl) 203, 224, 290 nm; $\lambda_{max}$(pH7.4) 293 nm; $\lambda_{max}$(0.1M NaOH) 298 nm. IR spectra of both 10 and 22 measured in KBr disks showed strong absorption at 1690 cm$^{-1}$, indicating that the lactam tautomer 10A is present in the solid state. The $^1$H-NMR was consistent with the benzotrizine structure, with all three aromatic ring-B protons deshielded ($\delta 8.10$) relative to the 3',5'-protons ($\delta 6.60$) and even the 2',6'-protons ($\delta 7.57$) on the phenyl ring. However, a more interesting feature of the $^1$H-NMR spectra of diester 22 and diacid 10 was the presence of upfield signals, at $\delta 1.7$ for 22 (in CDCl$_3$ solution) and at $\delta 2.1$ for 10 (in d$_6$-DMSO solution), which we believe arise from the lactim tautomeric form 10B in these non-aqueous solvents. Since the peak areas for these upfield signals in 10 and 22 closely approximated one proton, it appears that very little of the lactam 10A was present under aprotic conditions. The position of the lactam (10A)-lactim (10B) equilibrium presumably depends not only on the dielectric constant of the solvent, but also on its protic versus aprotic nature.

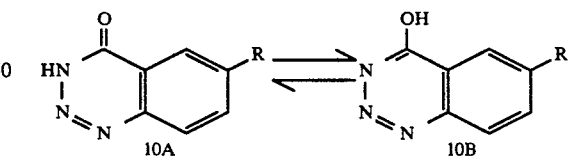

Biological Assays

The ability of 2-aza-2-desamino-5,8-dideazafolic acid (10) to inhibit purified TS from L1210 murine leukemic cells (using the assay described by Sikora et al., Biochem. Pharmacol. 37:4047, 1988, herein incorporated by reference), to serve as a substrate for partly purified FPGS from mouse liver (using the assay described by Moran et al., Mol. Pharmacol. 27:156, 1985, herein incorporated by reference), and to inhibit the growth of L1210 cells in culture (using the assay described by Rosowsky et al., J. Med. Chem. 34:461, 1991, herein incorporated by reference) was evaluated with the aim of comparing this compound with the analogous $N^{10}$- unsubstituted analogues of 5,8-dideazafolic acid (1) and 2-desamino-5,8-dideazafolic acid (3). The results are summarized in Table 1, along with published data for $N^{10}$-propargyl-5,8-dideazafolic acid (2, CB3717).

greater than that of either 5,8-dideazafolate or CB3717, and was comparable to that of 2-desamino-5,8-dideazafolate, the lead compound whose improved pharmacological properties relative to those of CB3717

TABLE 1

Biological Activity of 2-Aza-2-deaza-5,8-dideazafolic Acid (10) and Related Compounds

| Compound[a] | L1210 TS[b] $K_i$, 1—1 | Mouse liver FPGS[c] | | | L1210 cells[d] $IC_{50}$, μM |
|---|---|---|---|---|---|
| | | $K_m$, μM | $V_{max}$(rel) | k'(rel) | |
| 5,8-Dideazafolic Acid (1) | 0.067 | 6.4 | 1.3 | 29 | 2.7 |
| $N^{10}$-Propargyl-5,8-dideazafolic Acid (CB3717, 2) | 0.0027 | 40 | 0.88 | 2.3 | 3.5 |
| 2-Desamino-5,8-dideazafolic Acid (3) | 2.0 | 4.8 | 1.3 | 29 | 0.43 |
| 2-Aza-2-desamino-5,8-dideazafolic Acid (10) | 0.33 | 25 | 1.6 | 6.3 | 0.42[e] |

[a] With the exception of the $K_i$ for TS inhibition by 1, which is from Sikora et al. (Biochem. Pharmacol. 37:4047, 1988), all the data for the reference compounds 1-3 are from Jackman et al. (Cancer Res. 50:5212, 1990).
[b] Inhibition of purified TS from L1210 cells was determined by the $^3$H-release assay method as described previously (Sikora et al.)
[c] Substrate activity for partially purified FPGS from mouse liver was determined as described previously (Moran et al., Mol. Pharmacol. 27:156, 1985), with relative $V_{max}$ and k' values expressed in comparison with folic acid (1.0).
[d] Cells were incubated in RPMI 1640 medium supplemented with 10% non-dialyzed fetal calf serum, and were counted after 48 h of drug treatment.
[e] The $IC_{50}$ for cells grown in the presence of 10 μM dThd increased only to 0.84 μM.

As shown in Table 1, a $K_i$ of 0.33 μM was obtained for TS inhibition by 10, which compared very favorably with the values of 2.0 μM reported previously for the 2-desamino analogue 3 (Jackman et al., Cancer Res. 50:5212, 1990). Thus, replacement of $C^2$ and the attached $NH_2$ group by a nitrogen atom with a lone pair of electrons gave a ca. sixfold increase in TS binding. These results were consistent with our hypothesis that the structural change embodied in the general structure A might facilitate interaction with TS by allowing the A-ring to fit more snugly into the enzyme active site.

The $K_m$ of the polyglutamates of quinazoline TS inhibitors such as 1-3 to TS is known to decrease by as much as two orders of magnitude relative to the monoglutamates. It was therefore of interest to determine whether 10 is a substrate for FPGS, since a 100-fold increase in binding could bring the $K_m$ down to the low nanomolar range. As shown in Table 1, the $K_m$ of 10 for FPGS was found to be 25 μM, a value intermediate between those of aminopterin (18 μM) (Moran et al., Mol. Pharmacol. 27:156, 1985) and CB3717 (40 μM) (Jackman et al., Cancer Res. 50:5212, 1990), but higher than those of either 1 or 3, which were in the 5–10 μM range. The relative first-order rate constant, k'(rel), calculated by dividing $K_m$(app) into the $V_{max}$(rel), was found to be 6.3, a value twofold greater than that value for CB3717. However, the k'(rel) of 10 was 4.6-fold lower than the k'(rel) of 1 or 3, suggesting that it is somewhat more efficiently polyglutamylated by the enzyme than is CB3717, but less efficiently polyglutamylated than the two $N^{10}$-unsubstituted compounds included in the comparison. However, there was enough substrate activity to conclude that if 10 crossed the cell membrane, it would be converted into non-effluxing polyglutamates, and that if these polyglutamates bound tightly to TS (or other enzymes of the folate pathway), cell growth would be inhibited.

Incubation of L1210 cells with 10 showed that this compound was in fact a potent inhibitor of growth in culture, with an $IC_{50}$ of 0.42 μM as compared with 2.7 μM for 1, 3.5 μM for 2, and 0.43 μM for 3. Thus, the potency of 10 against cultured cells was 5- to 10-fold eventually led to development of the thiophene analogue 9 (Jodrell et al.; Marsham et al.).

An interesting feature of CB3717 and its 2-desamino analogues is that their inhibitory effect on the growth of L1210 cells is not fully reversed by 10 μM thymidine alone, but is restored to normal levels in the presence of either a combination of 10 μM thymidine (dThd) and 50 μM hypoxanthine (Hx) or a combination of 5 μM dThd and 5 μM folinic acid (Jackman et al., Cancer Res. 50:5212, 1990). This finding suggests that the intracellularly-formed polyglutamates of the quinazolines can inhibit not only TS but also DHFR, and that this results in depletion of tetrahydrofolate cofactor pools and inhibition of purine synthesis. It was therefore of interest to determine whether 2-aza analogues such as 10 also require both dThd and HX for complete protection from their growth inhibitory effect. When L1210 cells were grown in the presence of 5 μM dThd, an $IC_{50}$ of 0.84 μM was obtained for 10, as compared with a value of 0.42 μM when dThd was omitted from the medium. This twofold difference is comparable to that reported for 1 and 3, but much lower than that reported for 2 (Jackman et al.). Thus, the pattern of growth inhibition by 10 resembles that of 1 and 3, and suggests that this compound may not function solely at the level of thymidylate biosynthesis.

The potent activity of 2-aza-2-desamino-5,8-dideazafolate (10) against tumor cells in culture, its ability to bind efficiently to TS and FPGS, and its novel molecular structure and easy synthetic access suggest that the compounds of the invention are readily obtainable by the methods disclosed herein, and will prove to be effective antifolates with multiple enzyme targets.

EXPERIMENTAL

IR spectra were obtained on a Perkin-Elmer Model 781 double-beam recording spectrophotometer; only peaks above 1200 cm$^{-1}$ are reported. UV spectra were obtained on a Varian Model 210 instrument. $^1$H-NMR spectra were obtained on a Varian EM3460L spectrometer with Me$_4$Si or Me$_3$Si(CH$_2$)$_3$SO$_3$Na as the reference. TLC analyses were done on fluorescent Eastman 13181 silica gel sheets or Eastman 13254 cellulose sheets. Spots were visualized under 254-nm UV illumination. Column chromatography was done on Baker 3405 (60–200 mesh) silica gel or Whatman DE-52 pre-swollen DEAE-cellulose. Solvents in moisture sensitive reactions were dried over Linde 4A molecular sieves (Fisher, Boston, Mass.). HPLC was done on Waters $C_{18}$ radial compression cartridges (analytical: 5 μm particle size, 5×100 mm; preparative: 15 μm particle size, 25×100 mm). Melting points were determined in Pyrex capillary tubes in a Mel-Temp apparatus (Cambridge Laboratory Devices, Cambridge, Mass) and are not corrected. Microanalyses were performed by Robertson Laboratory, Madison, N.J.

6-Methyl-1,2,3-benzotriazin-4(3H)-one (15). A mixture of 5-methyl-2-nitrobenzoic acid (12) (36.2 g, 0.2 mol) and $SOCl_2$ (50 mL) was heated under reflux for 20 min, during which a homogeneous solution was obtained. After removal of the excess $SOCl_2$ with the aid of a water aspirator, the residue was dissolved in dry THF (40 mL) and the solution added dropwise with stirring to an ice-cold solution of NaOH (8 g, 0.2 mol) in 28% $NH_4OH$ (300 mL). The precipitate was collected, washed with water, and recrystallized from $EtOH-H_2O$ to obtain 5-methyl-2-nitrobenzamide (13) (31.5 g, 87%) as a white solid; mp 176°–177° C. [lit. (Findeklee, Ber. 38:3558, 1905) mp 176°–177° C.]; IR (KBr) V 1655 $Cm^{-1}$ (amide C=O). A solution of 13 (31.5 g, 0.175 mol) in MeOH (250 mL) was shaken With 5% Pd-C (0.5 g) under 3 atm. of $H_2$ for 24 h in a Parr apparatus. A solid formed after the initial heat of reaction subsided. The mixture was heated to boiling to redissolve the product, and was filtered while hot. The filtrate was evaporated under reduced pressure and the residue dried at 90° C. for 1 h (caution: some sublimation may occur) to obtain 2-amino-5-methylbenzamide (14) as a white solid (25.3 g, 96%); mp 173°–175° C. [lit. (Findeklee) mp 179° C.]; $^1$H-NMR ($CDCl_3$) δ6.60 (d, 1H, J=8 Hz, $C_3$-H). To an ice-cold suspension of 14 (25.3 g, 0.168 mol) in 3.6N HCl (260 mL) was added dropwise over 25 min a solution of $NaNO_2$ (12.75 g) in $H_2O$ (100 mL) while keeping the internal temperature below 5° C. After another 20 min of stirring at this temperature, 10N NaOH (100 mL) was added, causing all the solid to dissolve. The solution was acidified to pH 2 with 12N HCl and chilled. The solid was filtered and recrystallized from EtOH to obtain off-white needles (26.2 g, 97%); mp 217°–218° C. (dec, gas evolution) [lit. (Ferrand et al., Eur. J. Med. Chem. 2:337, 1987) mp 219°–220° C.]; IR (KBr) v 1680 (lactam C=O); $^1$H—NMR ($d_6$—DMSO+$D_2O$) δ3.30 (s, 3H, 6—Me), 8.00 (m, 3H, aryl); UV (95% EtOH) $\lambda_{max}$208, 225, 282 nm.

Dimethyl N-[4-(1,2,3-Benzotriazin-4(3H)-on-6-yl)methyl]aminobenzoyl-L-glutamate (22). N-Bromosuccinimide (1.37 g, 7.7 mmol) was added in a single portion to a solution of 14 (1.13 g, 7 mmol) in glacial AcOH (70 mL) in an oil bath at 60° C. The resulting solution was heated at 70° C. with illumination from a 150-watt floodlamp (General Electric) for 2 h. After evaporation of the solvent under reduced pressure, the residue was partitioned between $CHCl_3$ and $H_2O$. The $CHCl_3$ layer was washed with 5% $NaHCO_3$, rinsed with $H_2O$, and evaporated to obtain a product (0.946 g) which was estimated to consist of a 2:3 mixture of 6-bromomethyl-1,2,3-benzotriazin-4(3H)-one (20) [$^1$H—NMR ($CDCl_3$) δ4.63] and unchanged 15 [$^1$H—NMR ($CDCl_3$) δ3.30].

The entire mixture of 20 and 15 from the bromination reaction (estimated to contain 1.97 mmol of 20 from the δ4.63/δ3.30 ratio) was added in a single portion to a solution of dimethyl N-(4-aminobenzoyl)-L-glutamate (0.588 g, 2 mmol) (Koehler et al., J. Amer. Chem. Soc., 80:5779, 1958) in dry DMF (10 mL). Then, solid $NaHCO_3$ (0.168 g, 2 mmol) was added and the mixture was kept in an oil bath at 65° C. for 3 days. The solvent was evaporated under reduced pressure and the residue partitioned between $CHCl_3$ and $H_2O$. The $CHCl_3$ layer (TLC: $R_f$0.70, 0.65, 0.4, 0.0; silica gel, 19:1 $CHCl_3$-MeOH) was evaporated and the residue chromatographed on a silica gel column (45 g, 2.5×40 cm) with 20:1 $CHCl_3$—MeOH as the eluent. Pooled fractions containing the spot with $R_f$=0.4 were evaporated in two batches, and the residues were dried separately in vacuo ($P_2O_5$, 65° C.). The first batch (0.254 g, 28%) was TLC-homogeneous, whereas the other (0.154 g, 17%) contained a small impurity. Rechromatography of the TLC-homogeneous batch afforded analytically pure 10 as a beige powder (0.22 g, 87% recovery)); mp 94°–102° C.; IR (KBr) v 3430, 3040, 2960, 1740, 1690, 1640, 1615, 1580, 1515, 1445, 1420, 1335, 1285, 1265 $cm^{-1}$; NMR ($CDCl_3$) δ1.71 (br s, 1H, lactim OH), 2.43 (m, 4H, $CH_2CH_2$), 3.63 (s, 3H -COOMe), 3.75 (s, 3H, α-COOMe), 4.65 (m, 4H, $CH_2N$, NH, α-CH), 6.58 (d, J=9 Hz, 2H, 3'- and 5'-H), 7.68 (d, J=9 Hz, 2H, 2'- and 6'- H), 7.8-8.4 (m, 3H, aryl). Anal. Calcd for $C_{22}H_{23}N_5O_6$.0.6$H_2O$: C, 56.92; H, 5.25; N, 15.08. Found: C, 57.05; H, 5.00; N, 14.71.

N-[4-(1,2,3-Benzotriazin-4(3H)-on-6-yl)methyl] aminobenzoyl-L-glutamic Acid (10). A stirred cloudy solution of 22 (195 mg, 0.42 mmol) in MeOH (5 mL) was treated dropwise with 1N NaOH (5 mL) over 1 min. The solution quickly became homogeneous, and after another 5 min the pH wa adjusted to neutrality with HCl. The MeOH was evaporated under reduced pressure and the product purified by preparative HPLC (8% MeCN in 0.05M $NH_4OAc$, pH 6.9). Pooled pure fractions were concentrated by rotary evaporation and then freeze-dried. The residue was redissolved in $H_2O$ (15 mL) and the solution lyophilized again to obtain a pale-yellow solid (162 mg, 81%); mp ca. 150° C. (gas evolution after softening at 140°–145° C.); IR (KBr) v 3420, 3150, 3040, 2980, 1690, 1615, 1580, 1555, 1520, 1445, 1405, 1330, 1285, 1270 $cm^{-1}$; NMR ($d_6$-DMSO) δ2.10 (m, 5H, $CH_2CH_2$, lactim OH), 4.15 (m, 1H, α-CH), 4.57 (m, 2H, $CH_2N$), 6.60 (d, J=8 Hz, 3'- and 5'-H), 7.02 (m, 1H, NH), 7.57 (d, J=8 Hz, 2H, 2'- and 6'-H, with overlapped m, 1H, NH), 8.10 (m, 3H, aryl); UV (0.1M HCl) $\lambda_{max}$203 nm (ε27,700), 224 (27,600), 290 (12,300); $\lambda_{max}$ (pH 7.4 phosphate buffer) 216-218 nm (plateau, ε32,200), 293 (24,300); $\lambda_{max}$ (0.1M NaOH) 298 nm (ε25,300). Anal. Calcd for $C_{20}H_{19}N_5O_6$.0.75 $NH_3$.2$H_2O$: C, 50.66; H, 5.37; N, 16.98. Found: C, 50.40; H, 5.41; N, 16.80.

Synthesis of Other 2-Aza-2-desamino-5,8-dideazafolic Acid Analogues (General Procedure). A solution of 15 in glacial AcOH (ca. 50 mL/g) is treated with a single portion of N-bromosuccinimide (10% molar excess) and heated at 75° C. under a 75-watt lamp for 2 h. The reaction mixture is evaporated to dryness under reduced pressure, the residue is partitioned between $CHCl_3$ and 5% $NaHCO_3$, and the organic layer is evaporated. The resulting solid, consisting of a mixture of unreacted 15 and bromide 20, is dissolved directly in dry DMF (ca. 10 mL/g) and treated with an amount of the appropriate N-aroyl-L-glutamate diester (prepared, for example, as described by Jones et al., Eur. J. Cancer 17:11, 1981; and/or Marsham et al.) equimolar to that of bromide 20 estimated to be present in the crude bromination produce by analysis of the $^1$H—NMR spectru. Solid NaHCO$_3$ (50% excess) is also added, and the mixture is stirred at 65° C. for 70 h. The DMF is evaporated under reduced pressure, and the residue is partitioned between CHCl$_3$ and water, with enough glacial AcOH added to bring the pH to <6. The CHCl$_3$ layer is evaporated, and the product is chromatographed on a column of silica gel (40 g) which is eluted first with CHCl$_3$ followed by mixtures of CHCl$_3$ and MeOH (up to 10% as needed). Fractions are monitored by TLC (silica gel, CHCl$_3$ or CHCl$_3$—MeOH as needed), and appropriate fractions are pooled and evaporated. The residue, consisting of the diethyl ester of the 2-aza-2-desamino-5,8-dideazafolate analogue, is suspended in 50% EtOH, and a stoichiometric amount of 1N NaOH is added in an equal volume of water. After 15 min at room temperature, the mixture is filtered and the filtrate adjusted to pH 8 by careful dropwise addition of 1N HCl. The EtOH is evaporated under reduced pressure, any insoluble material present is removed by filtration, and the filtrate is placed on a DEAE-cellulose column (40 g, HCO$_3$-form). The column is washed first with water to remove salts and any residual benzotriazinone 15, and then with 0.4M NH$_4$HCO$_3$. Appropriate fractions are pooled and subjected to repeated freeze-drying to obtain the final product, typically as a hydrated ammonium salt.

Other compounds of the invention may be prepared by appropriate variations in the above procedure. For example, the moiety attached to the 6-position of the benzotriazinone can be varied by substituting an appropriate reagent for the N-aroyl-L-glutamate diester utilized above; preparation of such a reagent would be readily accomplished by a synthetic organic chemist of ordinary skil, utilizing procedures such as those described in Jones et al., j. Med. Chem. 29:1114, 1986; Jones et al., Eur. J. Cancer 17:11, 1981; and Marsham et al.

Other embodiments are within the following claims. What is claimed is:

1. A compound having the formula

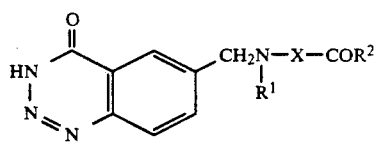

wherein X is thiophene, thiazole, pyridine, phenyl, or phenyl substituted with methyl, ethyl, or halogen;
R$^1$ is H, C$_1$-C$_4$ alkyl, C$_3$-C$_4$ alkenyl, or C$_3$-C$_4$ alkynyl; and
R$^2$ is OH, L-glutamic acid or L-aspartic acid.

2. The compound of claim 1, wherein X is thiophene, thiazole, pyridine, or

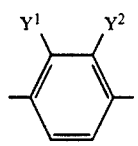

wherein each of Y$^1$ and Y$^2$, independently, is H, methyl, ethyl, or a halogen.

3. The compound of claim 2, wherein said Y$^1$ is H and said Y$^2$ is H, methyl, ethyl, F, Cl, or Br.

4. The compound of claim 2, wherein said X is

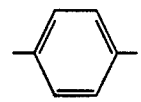

5. The compound of claim 1, wherein said R$^1$ is H, —CH$_3$, or —CH$_2$C≡CH.

6. The compound of claim 1, wherein said compound has the formula

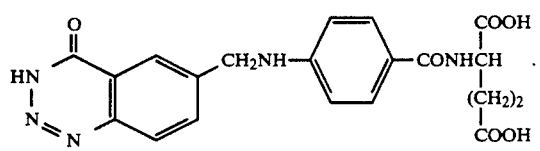

7. The compound of claim 1, wherein said compound has the formula

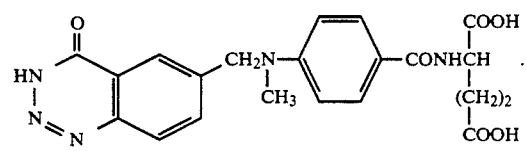

8. The compound of claim 1, wherein said compound has the formula

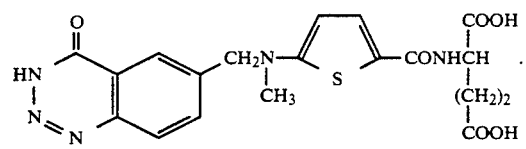

9. The compound of claim 1, wherein said compound has the formula

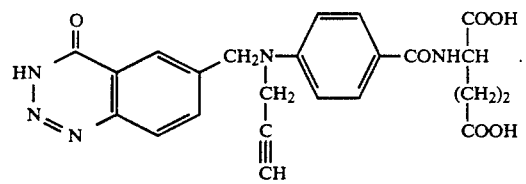

10. The compound of claim 1, wherein said compound has the formula

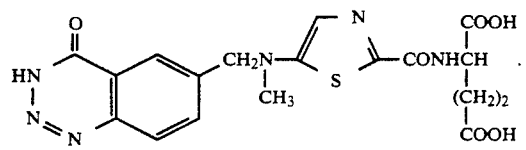

11. A therapeutic composition comprising an effective amount of the compound of claim 1 in a pharmaceutically-acceptable carrier.

* * * * *

UNITED STATES PATENT AND TRADEMARK OFFICE
CERTIFICATE OF CORRECTION

PATENT NO.  : 5,234,925

DATED       : August 10, 1993

INVENTOR(S) : Andre Rosowsky

It is certified that error appears in the above-identified patent and that said Letters Patent is hereby corrected as shown below:

Column 3, lines 15-33 change drawing to the following:

thiophene 

thiazole 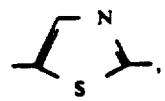

pyridine 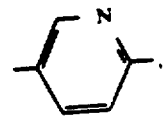

or substituted or unsubstituted phenyl 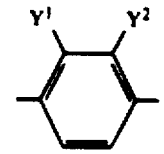

UNITED STATES PATENT AND TRADEMARK OFFICE
CERTIFICATE OF CORRECTION

PATENT NO.  : 5,234,925

DATED       : August 10, 1993

INVENTOR(S) : Andre Rosowsky

It is certified that error appears in the above-identified patent and that said Letters Patent is hereby corrected as shown below:

Column 5, line 15, "On" should be --on--.

Column 5, line 18, "benzoriazine" should be --benzotriazine--.

Column 6, line 11, "benzotrizinone" should be --benzotriazinone--.

Column 6, line 12, "spectru," should be --spectrum,--.

Column 6, line 22, "20" should be --22--.

Column 7, in Table 1, change "1-1" to --$\mu$M--.

Column 9, line 30, "With" should be --with--.

Column 9, line 50, "2:337," should be --22:337,--.

Column 9, line 58, "14" should be --15--.

UNITED STATES PATENT AND TRADEMARK OFFICE
CERTIFICATE OF CORRECTION

PATENT NO. : 5,234,925

DATED : August 10, 1993

INVENTOR(S) : Andre Rosowsky

It is certified that error appears in the above-identified patent and that said Letters Patent is hereby corrected as shown below:

Column 10, line 25, "65" should be --γ--.

Column 10, line 50, insert --(-- before "m,".

Column 11, line 4, "spectru" should be --spectrum--.

Column 11, line 39, "skil," should be --skill,--.

Column 11, line 40, "j." should be --J.--.

Signed and Sealed this

Twenty-fourth Day of May, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,234,925
DATED : August 10, 1993
INVENTOR(S) : Andre Rosowsky

It is certified that error appears in the above-indentified patent and that said Letters Patent is hereby corrected as shown below:

Figures

In Figure 1, Section (vii), "22,23: R1 = H, ME; $R^2$= H" should be --22,23: $R^1$ = H, Me; $R^2$= Me--.

Column 1, lines 37-38, delete "While this compound has many desirable evaluation."

Column 2, line 15, after "Chem." insert --). These--.

Column 2, lines 51-52, delete "from polyglutamylation of the more conventional 2-desamino".

Column 3, line 7, "$C_4C_4$" should be --$C_1C_4$--.

Column 3, line 8, "alkenyl" should be --alkynyl--.

Column 3, line 9, "$CH_2C=CH$" should be --$CH_2C\equiv CH$--.

Column 3, line 12, delete "thiophene".

Signed and Sealed this

Twenty-third Day of January, 1996

Attest:

BRUCE LEHMAN

Attesting Officer    Commissioner of Patents and Trademarks